United States Patent [19]

Trivedi et al.

[11] Patent Number: 4,791,103

[45] Date of Patent: Dec. 13, 1988

[54] 2,N6-DISUBSTITUTED ADENOSINES, DERIVATIVES AND METHODS OF USE

[75] Inventors: Bharat K. Trivedi, Canton; Walter Moos, Ann Arbor; Harriet W. Hamilton; William C. Patt, both of Chelsea, all of Mich.

[73] Assignee: Warner-Lambert Company, Morris Plains, N.J.

[21] Appl. No.: 771,590

[22] Filed: Sep. 5, 1985

Related U.S. Application Data

[63] Continuation-in-part of Ser. No. 700,141, Feb. 8, 1985, and Ser. No. 665,218, Oct. 16, 1984.

[51] Int. Cl.⁴ .................... A01N 31/00; A61K 31/70; C07H 19/06; C07H 19/16

[52] U.S. Cl. .......................... 514/46; 514/47; 536/24; 536/26; 536/27; 536/28

[58] Field of Search .......... 536/26, 24, 27, 28; 514/46, 47

[56] References Cited

FOREIGN PATENT DOCUMENTS 0152944 8/1985 European Pat. Off. .............. 514/46

Primary Examiner—Ronald W. Griffin
Assistant Examiner—L. Eric Crane
Attorney, Agent, or Firm—Joan Thierstein

[57] ABSTRACT

Novel N6-substituted adenosines having desirable ratio of affinities at A1 or A2 receptors and highly desirable central nervous system and cardiovascular activities, such as analgesic, antipsychotic, sedative, or antihypertensive as well as immunoinflammatory activity.

48 Claims, No Drawings

4,791,103

2,N⁶-DISUBSTITUTED ADENOSINES, DERIVATIVES AND METHODS OF USE

BACKGKROUND OF THE INVENTION

This is a continuation in part of U.S. patent application Ser. No. 700,141 filed February 8, 1985 and U.S. patent application Ser. No. 665218 filed Oct. 16, 1984.

U.S. Pat. No. 3,922,261 describes $N^6$-(2-tetrahydronaphthyl)adenosine for lowering serum lipoprotein, free fatty acid and triglyceride levels and increasing coronary flow without altering arterial blood pressure or cardiac frequency. The present invention describes $N^6$-(1-tetrahydronaphthyl)-adenosines, $N^6$-(benzocycloalkyl)-, and $N^6$-(benzocycloalkylenyl)-alkyl adenosines having neuroleptic activity and antihypertensive properties.

Various adenosine derivatives are claimed having desirable ratio of affinities at A1 or A2 receptors and highly desirable central nervous system and cardiovascular activities, such as analgesic, antipsychotic, sedative, or antihypertensive, as well as immunoinflammatory activity in copending applications. However, in each case the substituents of the applications do not teach the $N^6$-benzocycloalkylmethyl and $N^6$-benzocycloalkylenylmethyl- adenosines of the present invention. For example, U.S. Ser. No. 665,219 discloses $N^6$-tricyclicadenosines, U.S. Ser. No. 665,195 discloses $N^6$-acenaphthyladenosines, U.S. Ser. No. 665,197 discloses $N^6$-benzopyrano- and benzothiopyrano- adenosines, U.S. Ser. No. 665,218 discloses $N^6$-tetrahydronaphthyladenosines now combined herewith U.S. Ser. No. 700,141 disclosing related $N^6$-benzocycloalkylmethyl and benzocycloalkylenemethyl adenosines, U.S. Ser. No. 665,216 discloses $N^6$-bicyclo[2.2.1]heptyladenosines, U.S. Ser. No. 665,229 discloses $N^6$-dihydropypropyladenosines, U.S. Ser. No. of 665,230 10-26-84 discloses (S)-$N^6$-2-hydroxypropyladenosines, U.S. Ser. No. 665,217 discloses $N^6$-substituted deoxyribose adenosines, U.S. Ser. No. 665,233 discloses $N^6$-substituted-5'-deoxy-5'chloro adenosines, and U.S. Ser. No. 665,232 discloses $N^6$-substituted-5'-methylthio adenosines.

Additionally, British 1,529,721 discloses various $N^6$-heterocyclic adenosines as antiproliferative and coronary circulation active agents. French 6650M (Derwent No. 37,912) discloses $N^6$-alkyl-, -aryl-, -aralkyl-, -furfuryl-, and -thienyl- adenosines for use as antiinflammatory agents. German No. 2,139,107 discloses numerous $N^6$-substituted alkyladenosines including alkyl, aralkyl, and benzoheterocyclic fused rings.

More particularly, German Patent No. 2,139,107 discloses $N^6$-[decalinyl, tetralinyl, quinolinyl, and isoquinolinyl]methyladenosines having coronary and circulatory properties. Also particularly, German Patent No. 1,670,116 discloses $N^6$-naphthylmethyladenosines having circulatory activity. Further, copending U.S. Ser. No. 558,144 now U.S. Pat. Ser. No. 4,501,735 discloses benzocycloalkyladenosines in which the benzocycloalkyl attaches directly to the adenosine residue. Finally, Merck discloses in German No. 2,402,804 a tetralinyladenosine differing with respect to the tetralinyl of the above noted U.S. Ser. No. 558,144 by the position on the tetralinyl group to which the adenosine is attached. Utility in German No. 2,402,804, is also increased coronary flow and oxygen content, as well as, lower blood lipoprotein levels, inhibition of thrombocyte aggregation and fibrinolytic activity.

The compounds having the Formula I defined hereinafter as the instant invention are adenosine analogs having some of the same activity as adenosine, but having a significantly longer duration of action. A distinguishing feature of these compounds from other adenosine analogs previously described, is the discovery that the $N^6$-(1-tetrahydronaphthyl), benzocycloalkyl- and benzocycloalkylene methyl adenosines of formula I of the present invention have favorable ratio of affinities at A1 and A2 receptors and highly desirable central nervous system and cardiovascular activities, such as analgesic, antipsychotic, sedative, or antihypertensive. In addition, these adenosine compounds also have immunoinflammatory activity.

SUMMARY OF THE INVENTION

Accordingly, the present invention relates to a compound of the Formula I wherein $R_1$ is of the Formula II or III, wherein n is one to four; Z is hydrogen, lower alkyl, or hydroxy; Y is (a) hydrogen, (b) lower alkyl, or (c) OR wherein R is hydrogen, lower alkyl or lower alkanoyl; A is a bond or a straight or branched alkylene of one to four carbon atoms with the proviso that A cannot be a bond when $R_1$ is of Formula II and n is one; X and X' are each independently (a) hydrogen, (b) lower alkyl, (c) lower alkoxy, (d) hydroxy, (e) lower alkanoyl, (f) nitro, (g) trifluoromethyl, (h) halogen, (i) amino, (j) monoloweralkyl- or diloweralkylamino, or (k) X and X' taken together are a methylenedioxy group; $R_2$ is (a) hydrogen, (b) halogen, (c) NR'R'' wherein R' and R'' are independently hydrogen, lower alkyl, phenyl or phenyl substituted by lower alkyl, lower alkoxy, halogen, or trifluoromethyl, or (d) SR''' wherein R''' is hydrogen, lower alkyl, lower alkanoyl, benzoyl or phenyl $R'_2$, $R'_3$, and $R'_5$ are each independently (a) hydrogen, (b) alkanoyl having two to twelve carbon atoms in a straight or branched alkyl chain, (c) benzoyl or (d) benzoyl substituted by lower alkyl, (e) lower alkoxy, (f) halogen or (g) $R'_2$ and $R'_3$ taken together form a five-membered alkylidene ring having a total of up to twenty carbons such as for example, isopropylidene; and $R'_5$ may be a phosphate, hydrogen or dihydrogen phosphate, or an alkali metal or ammonium, or dialkali or diammonium salt thereof such as for example $PO_3Na_2$; its diastereomer; or a pharmaceutically acceptable acid addition salt thereof; with the proviso that when $R_1$ is II, A is a branched or straight alkylene of one to four carbon atoms, and X, X', Z, and Y are hydrogen or lower alkyl, then n cannot be two.

The present invention also relates to a pharmaceutical composition comprising a therapeutically effective amount of a compound of the above Formula I with a pharmaceutically acceptable carrier, and to a method of treating mammals by administering to such mammals a dosage form of a compound of the Formula I as defined above.

DETAILED DESCRIPTION OF THE EMBODIMENTS

In the compounds of the formula I, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy is O-alkyl of from 1 to 6 carbon atoms as defined above for "lower alkyl".

Lower alkanoyl is a straight or branched

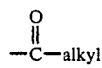

group of from 1 to 6 carbon atoms in the alkyl chain as defined above.

The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain asymmetric carbon atoms. The invention includes the individual diastereomers and mixtures thereof. The individual diastereomers may be prepared or isolated by methods known in the art.

A preferred embodiment of the present invention is a compound of the Formula I where in $R_1$ is of Formula II and Z is hydrogen, A is a straight or branched alkylene of one to four carbon atoms, n, Y, X, X', $R_2$, $R'_2$, $R'_3$, and $R'_5$ are as defined above.

Another preferred embodiment of the present invention is a compound of Formula I, wherein $R_1$ is of Formula II; Z is hydrogen, A is a straight or branched alkylene of one to four carbon atoms, X, X', and Y are hydrogen and n, $R_2$, $R'_2$, $R'_3$, and $R'_5$ are as defined above.

Another preferred embodiment is a compound of Formula I wherein $R_1$ is of Formula II, Z is hydrogen, A is a straight or branched alkylene of one to four carbon atoms, X, X', and Y are hydrogen; n is equal to 1, and $R_2$, $R'_2$, $R'_3$, and $R'_5$ are as defined above.

Still another preferred embodiment is a compound of formula I wherein $R_1$ is of Formula II; Z is hydrogen, A is a straight or branched alkylene of one to four carbon atoms, X, X', and Y are hydrogen; n=1; $R_2$ is a) hydrogen, (b) halogen, (c) NR'R'' wherein R' and R'' are independently hydrogen, lower alkyl or phenyl, or (d) SR wherein R is hydrogen, lower alkyl or phenyl; and $R'_2$, $R'_3$, and $R'_5$ are as defined above.

Still another preferred embodiment is a compound of Formula I. Wherein $R_1$ is of Formula II; X, X', Z, and Y are hydrogen, n is one, $R_2$ is hydrogen, chlorine, or amino; A is methylene and $R'_2$, $R'_3$, and $R'_5$ are as defined above.

A further preferred embodiment is a compound of Formula I wherein $R_1$ is of Formula II; X, X', Z, and Y are hydrogen; $R_2$ is hydrogen, chlorine, or amino; A is methylene; and $R'_2$, $R'_3$, and $R'_5$ are hydrogen.

A particular embodiment includes $N^6$-[1-indanyl methyl]adenosine.

Another embodiment of the present invention is a compound of Formula I, wherein $R_1$ is of Formula III and A is straight or branched alkylene of one to four carbon atoms, X, X', n, $R_2$, $R'_2$, $R'_3$, and $R'_5$ are as defined above.

Therefore, another preferred embodiment of the present invention is a compound of formula I wherein $R_1$ is of Formula III; A is a straight or branched alkylene of one to four carbon atoms, X, X', and Y are hydrogen, n is one, and $R_2$, $R'_2$, $R'_3$, and $R'_5$ are as defined above.

Another preferred embodiment of the present invention is a compound of formula I wherein $R_1$ is Formula III; A is a straight or branched alkylene of one to four carbon atoms, X, X' are hydrogen; n is one, $R_2$ is (a) hydrogen, (b) halogen, (c) NR'R'' where R' and R'' are each independently hydrogen, lower alkyl or phenyl, or (d) SR where R is hydrogen, lower alkyl, or phenyl; $R'_2$, $R'_3$, and $R'_5$ are as defined above.

Still another preferred embodiment of the present invention is a compound of Formula I wherein $R_1$ is of Formula III; X and X' are hydrogen; n is one; $R_2$ is hydrogen, halogen, or amino; A is methylene; and $R'_2$, $R'_3$, and $R'_5$ are as defined above.

A further preferred embodiment is a compound of Formula I where $R_1$ is of Formula III; X and X' are hydrogen; n is one; $R_2$ is hydrogen, halogen, or amino, A is methylene; and $R'_2$, $R'_3$, and $R'_5$ are hydrogen.

A particular embodiment of the Formula I wherein $R_1$ is of Formula III includes $N^6$-[1H-inden-3-ylmethyl]adenosine.

A preferred embodiment is a compound of Formula I wherein X, $X^1$, and Y are hydrogen, $R_1$ is of Formula II where A is a bond, and n is 2, and Z, $R_2$, $R_2'$, $R_3'$, and $R_5'$ are as defined above.

Another preferred embodiment is a compound of Formula I wherein X, $X^1$, and Y are hydrogen; $R_1$ is of Formula II where A is a bond, n is 2, and Z is hydrogen or lower alkyl, and $R_2$, $R_2'$, $R_3'$, and $R_5'$ are as defined above.

Still another preferred embodiment is a compound of Formula I wherein X, $X_1$, and Y are hydrogen; $R_1$ is of Formula II where A is a bond, n is 2, and one of X or $X_1$ is hydrogen or lower alkyl; $R_2$ is hydrogen, and Z, $R_2'$, $R_3'$, and $R_5'$ are as defined above.

Another preferred embodiment is a compound of formula I wherein X and Y are hydrogen; $R_1$ is of Formula II where A is a bond, Z is hydrogen or lower alkyl; $R_2$ is hydrogen, and $R_2'$, $R_3'$, and $R_5'$ are each independently hydrogen, acetyl or benzoyl, or $R_2'$ and $R_5'$ when taken together are isopropylidene.

A further preferred embodiment is a compound of formula I, wherein X, and Y are hydrogen; $R_1$ is of Formula II where A is a bond, Z is hydrogen or lower alkyl; $R_2$ is hydrogen, and $R_2'$, $R_3'$, and $R_5'$ are hydrogen.

A particular embodiment includes $N^6$-(1-tetrahydronaphthyl)adenosine or a pharmaceutically acceptable salt thereof.

It is now found that the compounds of Formula I wherein $R_1$ is II, X, X', Z, and Y are hydrogen, A is methylene; $R_2$, $R'_2$, $R'_3$, and $R'_5$ are all hydrogen and n is 1 provides unexpectedly superior affinities for A1 and A2 receptors.

The compounds of formula I may be conveniently synthesized by reacting a 6-halopurine riboside of Formula IV with the $N^6$-(benzocycloalkyl)- and $N^6$-(benzocycloalkylene)-alkyl amine or requisite tetrahydronaphthyl amine of the compounds shown as either Formula V or Formula VI in an inert solvent such as alcohol, or an aprotic solvent such as dimethylformamide between about 25° to about 130° C. for from 1–48 hours. It is useful to add a base such as triethylamine, or calcium carbonate to neutralize the hydrogen halide formed as a byproduct of the reaction, but this can also be accomplished by using an extra equivalent of the amine. It is also convenient, although not necessary, to protect the ribofuranose hydroxyl groups as acetate or benzoate esters which can be removed with ammonium hydroxide or sodium methoxide following the synthesis of the $N^6$ substituted adenosine. The reaction is illustrated in Scheme I having Formula IV, V, and VI wherein Hal is halogen, preferably chlorine or bromine, and A, X, Y, Z, n, $R_2$, $R_2'$, $R_3'$, and $R_5'$ are as defined for Formula I.

In addition, compounds of formula I wherein $R_2$ is other than hydrogen or halogen, may also be prepared from 2,6-dichloropurine riboside triacetate of formula IVa in a stepwise manner, by first reacting a compound of the formula IV with the requisite amine corresponding to formula IV or V to give a compound of formula VI, followed by replacing the chlorine atom at $C_2$ with the group $R_2$ using nucleophilic displacement conditions, and removing the protecting groups. See Scheme II.

The requisite amine starting materials or materials from which the amines can be prepared are available commercially or are prepared using methods known in the literature.

The compounds of Formula I have been found to possess differing affinities for adenosine receptors (designated $A_1$ and $A_2$ receptors for convenience). These compounds are active in animal tests which are predictive of neuroleptic activity for the treatment of major psychoses such as schizophrenia.

The compounds of the invention also have sedative/hypnotic properties and as such, are useful for the treatment of sleep disorders. These compounds also have analgesic properties and as such, are useful in the treatment of pain.

In addition, the compounds of the present invention are useful as antihypertensive agents for the treatment of high blood pressure.

PHARMACOLOGICAL EVALUATION

Adenosine Receptor Binding - $A_1$ Receptor Affinity (RBA1)

Preparation of Membranes

Whole brain minus cerebellum and brainstem from male Long Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (pmoles/gram of tissue) versus [bound radioligand/free radioligand]. Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the [bound radioligand/$B_{max}$ − bound radioligand]. The maximal number of binding sites ($B_{max}$) was calculated from the Scatchard plot.

Adenosine Receptor Binding - $A_2$ Receptor Affinity (RBA2)

Tissue Preparation

Brains from 200–500 g mixed sex Sprague-Dawley rats were purchased from Pel-Freez (Rogers, Arkansas). Fresh brains from male Long-Evans hooded rats (Blue Spruce Farms, Altamont, NY) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000 xg for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM $N^6$-cyclopentyladenosine (to eliminate $A_1$ receptor binding), 10 mM $MgCl_2$, 0.1 units/ml of adenosine deaminase and 1% dimethylsulfoxide. $N^6$-Cyclopentyladenosine was dissolved at 10 mM in 0.02

N HCl and diluted in Tris. Stock solutions and dilutions of $N^6$cyclopentyladenosine could be stored at $-20°$ C. for several months. Test compounds were dissolved at 10 mM in dimethylsulfoxide on the same day as the experiment, and diluted in dimethylsulfoxide to 100x the final incubation concentration. Control incubations received an equal volume (10 μl) of dimethylsulfoxide; the resulting concentration of dimethylsulfoxide had no effect on binding. [$^3H$]NECA was diluted to 40 nM in Tris. The membrane suspension (5 mg/0.79 ml) contained sufficient $MgCl_2$ and adenosine deaminase to give 10 mM and 0.1 units/ml, respectively, final concentration in the incubation. For test compounds with $IC_{50}$ values less than 1 μM, the order of additions was test compound (10 μl), $N^6$-cyclopentyladenosine (100 μl), [$^3H$]NECA (100 μl), and membranes (0.79 ml). For test compounds with IC50 values greater than 1 μM and limited water solubility, the order of additions (same volumes) was test compound, membranes, $N^6$-cyclopentyladenosine, and [$^3H$]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM $N^6$-cyclopentyladenosine, and specific binding was defined as total binding minus nonspecific binding. The $IC_{50}$ was calculated by weighted nonlinear least squares curve-fitting to the mass-action equation.

$$Y = T - S \cdot \frac{D}{D + K}$$

Weighting factors were calculated under the assumption that the standard deviation was proportional to the predicted value of Y. Nonspecific binding was treated as a very large (infinite) concentration of drug in the computer analysis. The $IC_{50}$ values (nM) for adenosine $A_1$ and $A_2$ receptor affinity are reported in the table.

| Example Number | RBA-1 (nM) | RBA-2 (nM) |
| --- | --- | --- |
| 1 | 59 | 476 |
| 2 | 44 | 243 |
| 3 | 403 | 2030 |
| 4 | 19 | 524 |
| 5 | 40 | 918 |
| 6 | 126 | 4370 |
| 7 | 42 | 324 |
| 8 | 21 | 407 |
| 9 | 4550 | 50500 |
| 10 | 19 | 217 |
| 11 | 444 | 2610 |
| 12 | 22400 | — |
| 13 | 1060 | 7920 |
| 14 | 8220 | 57100 |
| 15 | 500 | 4440 |
| 16 | 36 | 260 |
| 17 | 71 | 238 |
| 18 | 20 | 366 |
| 20 | 5840 | 46700 |
| 21 | 9 | 99 |
| 22 | 57 | 65.5 |
| 23 | 108 | 2850 |
| 24 | 159 | 76.5 |
| 25 | 120 | 987 |
| 26 | 713 | 2700 |
| 27 | 445 | 4010 |
| 28 | 208 | 1270 |

ANTIPSYCHOTIC EVALUATION

The compounds of the invention are new chemical substances which are useful as pharmaceutical agents for the treatment of psychoses. The antipsychotic activity of representative compounds of the invention was established by the Mouse Activity and Screen Test Procedure (MAST) described below.

Animals

Nine unfasted Swiss-Webster male mice weighing 20-30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing

A two part testing procedure is started one hour postinjection. First, the screen test (ST) is performed (see *Pharmac. Biochem. Behav.* 6, 351–353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (*Life Sciences*, 22, 1067–1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data:

The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion (LI) are based upon data accumulated for one hour. Both phases of testing are graded: A=60-100%;

C=31-59%; and N=0-30%. An overall dose rating is obtained by the following criteria:

| Inhibition of Locomotion Rating | with | Screen Test Failure Rating | = | Dose Rating |
|---|---|---|---|---|
| A | — | N or C | = | A |
| A | — | A | = | C |
| C | — | N or C | = | C |
| All other combinations | | | = | N |

LAD refers to the lowest dose at which an A rating is achieved. Compounds which exhibit an overall dose rating of A at a dose of 100 milligrams/kilogram or less are considered active. Utilizing this procedure, an overall dose rating of A was obtained for the noted compound at the indicated dose. The compounds are identified in the Examples.

| Example | Dose (mg/kg) | Inhibition of mouse locomotor activity | Screen test failure |
|---|---|---|---|
| 1 | 1 | 86% | 0% |
|   | 3 | 93% | 0% |
|   | 10 | 98% | 22% |
|   | 30 | 97% | 22% |
|   | 100 | 99% | 99% |
| 2 | 0.1 | 25% | 0% |
|   | 0.3 | 45% | 0% |
|   | 1.0 | 79% | 11% |
|   | 3.0 | 95% | 22% |
|   | 9.0 | 97% | 33% |
|   | 30.0 | 99% | 66% |
| 3 | 0.1 | 40% | 11% |
|   | 0.3 | 34% | 0% |
|   | 1.0 | 30% | 22% |
|   | 3.0 | 69% | 0% |
|   | 10 | 95% | 0% |
|   | 30 | 96% | 11% |
| 4 | 0.03 | 3% | 0% |
|   | 0.1 | 1% | 0% |
|   | 0.3 | 70% | 11% |
|   | 10 | 97% | 77% |
|   | 30 | 99% | 88% |
|   | 100 | 99% | 77% |
| 5 | 1 | 39% | 0% |
|   | 3 | 82% | 11% |
|   | 10 | 91% | 11% |
| 6 | 1 | 22% | 0% |
|   | 3 | 3% | 0% |
|   | 10 | 62% | 0% |
|   | 30 | 94% | 44% |
|   | 100 | 99% | 44% |
| 7 | 0.3 | 7% | 0% |
|   | 1.0 | 22% | 0% |
|   | 3.0 | 91% | 11% |
|   | 10 | 97% | 22% |
|   | 30 | 99% | 66% |
| 8 | 0.3 | 25% | 11% |
|   | 1.0 | 83% | 11% |
|   | 3.0 | 88% | 11% |
|   | 10.0 | 93% | 22% |
|   | 30.0 | 94% | 65% |
| 9 | 3 | −35% | 11% |
|   | 10 | −11% | 0% |
|   | 30 | −3% | 11% |
| 10 | 0.3 | −19% | 11% |
|   | 1.0 | 65% | 22% |
|   | 3.0 | 88% | 22% |
|   | 10.0 | 95% | 44% |
|   | 30.0 | 97% | 66% |
| 12 | 3 | 3% | 0% |
|   | 10 | −1% | 0% |
|   | 30 | −16% | 0% |
| 14 | −1 | 54% | 0% |
|   | 3 | 69% | 0% |
|   | 10 | 94% | 0% |
|   | 30 | 94% | 22% |
| 15 | 0.3 | 46% | 11% |
|   | 1.0 | 87% | 22% |
|   | 3.0 | 96% | 22% |
|   | 10.0 | 98% | 55% |
|   | 30.0 | 99% | 55% |
| 16 | 3 | −13% | 0% |
|   | 10 | 23% | 0% |
|   | 30 | 89% | 0% |
| 17 | 3 | 44% | 0% |
|   | 10 | 88% | 0% |
|   | 30 | 91% | 22% |
| 18 | 1 | 44% | 11% |
|   | 3 | 73% | 11% |
|   | 10 | 91% | 0% |
|   | 30 | 96% | 0% |
| 19 | 1 | 42% | 11% |
|   | 3 | 57% | 0% |
|   | 10 | 91% | 0% |
|   | 30 | 95% | 11% |
| 21 | 0.3 | −19 | 0 |
|   | 1.0 | 23 | 0 |
|   | 3.0 | 61 | 0 |
|   | 10.0 | 82 | 22 |
|   | 30.0 | 99 | 55 |
| 22 | 0.1 | 30 | 0 |
|   | 0.3 | 38 | 11 |
|   | 1.0 | 76 | 0 |
|   | 3.0 | 76 | 22 |
|   | 10.0 | 96 | 11 |
|   | 30.0 | 97 | 55 |
| 23 | 3.0 | 19 | 0 |
|   | 10.0 | 16 | 0 |
|   | 30.0 | 77 | 22 |
| 24 | 0.3 | 9 | 0 |
|   | 1.0 | 34 | 0 |
|   | 3.0 | 67 | 22 |
|   | 10.0 | 94 | 22 |
|   | 30.0 | 95 | 11 |
| 25 | 3.0 | −14 | 11 |
|   | 10.0 | 89 | 22 |
|   | 30.0 | 88 | 66 |
| 26 | 3.0 | 50 | 0 |
|   | 10.0 | 31 | 22 |
|   | 30.0 | 64 | 22 |
| 27 | 3.0 | 1 | 0 |
|   | 10.0 | 33 | 11 |
|   | 30.0 | 33 | 0 |
| 28 | 3.0 | 35 | 0 |
|   | 10.0 | 19 | 11 |
|   | 30.0 | 59 | 0 |

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A Method for the Direct Monitoring of Aortic Blood Pressure and Heart Rate from Conscious Rats The continuous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method

Cannulation Procedure:

Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3–0 green braided suture). The midline incision was closed in two steps (muscle first, skin second) using continuous over-and over sutures (4–0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel) were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, MA) by means of PE100 tubing. While on test, each rat received a continuous slow infusion of heparinized saline solution (approximately 400 1 or 40 units of heparin per 24 hour period) to prevent clot formation. Additional "flushes" of the cannula with heparinized saline were carried out when the aortic pulse pressure (systolic minus diastolic) was less than 25 mm Hg.

CADCS

The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main reserach computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22–26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressures.

When tested by the above procedure, compounds of examples as noted produced the following changes in MAP (mean arterial pressure) and heart rate. LAD refers to the lowest dose tested at which a >10% reduction in blood pressure for four consecutive hours is achieved.

Antihypertensive Evaluation

| Example Number | mg/kg | | Hour 1 | Hour 3 | Hour 5 | Hour 7 | Hour 9 |
|---|---|---|---|---|---|---|---|
| 1 | 1.0 | MAP | ↓18% | ↓13% | ↓14% | ↓14% | ↓3% |
|   |     | HR  | ↑12% | ↑11% | ↑10% | ↑7% | ↑15% |
|   | 10  | MAP | ↓51% | ↓41% | ↓36% | ↓25% | ↓22% |
|   |     | HR  | ↓24% | ↓14% | ↓2% | ↑6% | 0% |
| 2 | 3   | MAP | ↓46% | ↓32% | ↓32% | ↓32% | ↓30% |
|   |     | HR  | ↓9% | ↓1% | ↑2% | ↓5% | ↓5% |
| 3 | 10  | MAP | ↓28% | ↓23% | ↓18% | ↓16% | ↓13% |
|   |     | HR  | ↓3% | ↓4% | 0% | ↓3% | ↓3% |
| 4 | 10  | MAP | ↓50% | ↓32% | ↓21% | ↓22% | ↓21% |
|   |     | HR  | ↓45% | ↓28% | ↓3% | ↓10% | ↓11% |
| 5 | 3   | MAP | ↓28% | ↓18% | ↓15% | ↓10% | ↓5% |
|   |     | HR  | 0% | ↑4% | ↑8% | ↑3% | ↑17% |
|   | 10  | MAP | ↓55% | ↓42% | ↓32% | ↓26% | ↓17% |
|   |     | HR  | ↓40% | ↓31% | ↓17% | ↓3% | ↓3% |
| 6 | 10  | MAP | ↓30% | ↓5% | ↓4% | ↓9% | ↓11% |
|   |     | HR  | ↓3% | ↓3% | ↑6% | ↑9% | ↑12% |
| 7 | 3   | MAP | ↓52% | ↓46% | ↓44% | ↓35% | ↓36% |
|   |     | HR  | ↓24 | ↓25% | ↓28% | ↓8% | ↓11% |
| 8 | 10  | MAP | ↓44% | ↓16% | ↓12% | ↓2% | ↑5% |
|   |     | HR  | ↓8% | ↑13% | ↑12% | ↑21% | ↑26% |
| 9 | 3   | MAP | ↓9% | ↓8% | ↓9% | ↓12% | ↓8% |
|   |     | HR  | ↓12% | ↓5% | ↓2% | ↓4% | ↑5% |
| 10 | 3  | MAP | ↓37% | ↓29% | ↓28% | ↓27% | ↓24% |
|   |     | HR  | ↑7% | ↓5% | ↑3% | ↑4% | ↓6% |
| 13 | 10 | MAP | ↓48% | ↓42% | ↓44% | ↓48% | ↓44% |
|   |     | HR  | ↓34% | ↓34% | ↓33% | ↓28% | ↓22% |
| 14 | 10 | MAP | ↓38% | ↓11% | ↓12% | ↓9% | ↓12% |
|   |     | HR  | ↓6% | ↑17% | ↑15% | ↑9% | ↑9% |
| 15 | 1  | MAP | ↓19% | ↓5% | ↓8% | ↓2% | ↓13% |
|   |     | HR  | ↑8% | ↑20% | ↑16% | ↑28% | ↑20% |
| 16 | 3  | MAP | ↓2% | ↓2% | ↓1% | ↓1% | ↓2% |
|   |     | HR  | ↑2% | ↓7% | ↓1% | ↓3% | 0% |
| 17 | 3  | MAP | ↓8% | η14% | ↓14% | ↓10% | ↓12% |
|   |     | HR  | ↓3% | ↓10% | ↓2% | ↓1% | ↓8% |
| 19 | 10 | MAP | ↓35% | ↓28% | ↓25% | ↓22% | ↓15% |
|   |     | HR  | ↓7% | ↓10% | ↓4% | ↑1% | ↑5% |
| 20 | 10 | MAP | ↓51% | ↓38% | ↓38% | ↓33% | ↓29% |
|   |     | HR  | ↓30% | ↓29% | ↓21% | ↓14% | ↓15% |
| 21 | 3  | MAP | ↓27% | ↓17% | ↓17% | ↓6% | ↓4% |
|   |     | HR  | ↓3% | ↑14% | ↑10% | ↑16% | ↑12% |
|   | 10 | MAP | ↓40% | ↓32% | ↓27% | ↓25% | ↓22% |
|   |     | HR  | ↓15% | ↓4% | ↑1% | ↓3% | ↑2% |
| 23 | 10 | MAP | ↓5% | ↓10% | ↓9% | ↓1% | ↓12% |
|   |     | HR  | ↓1% | ↓2% | ↑7% | ↑27% | ↑3% |
| 24 | 10 | MAP | ↓39% | ↓39% | ↓37% | ↓37% | ↓30% |
|   |     | HR  | ↑13% | ↑11% | ↑16% | ↑16% | ↑14% |

MAP = Mean Arterial Pressure
HR = Heart Rate

ANALGESIC EVALUATION

The antiwrithing (AW) test provides preliminary assessment of compounds with potential analgesic activity. The test is performed in male SwissWebster mice. Compounds are administered subother appropriate vehicles in volumes of 10 ml/kg. Dosages represent active moiety.

Acetic acid (0.6%, 10 ml/kg) is injected intraperitoneally 20 minutes after administration of the adenosine agonist. Writhing movements are counted for five minutes starting seven minutes after the acetic acid injection. Writhing is defined as abdominal constriction and stretching of the body and hind legs with concave arching of the back. Data are expressed as ED50 values, where the $ED_{50}$ is the dose necessary to suppress writhing by 50% relative to vehicle controls. ED50 values are calculated by nonlinear regression analysis.

IMMUNOIN-FLAMMATORY EVALUATION

An assessment of potential antiinflammatory or immunoinflammatory activity is provided by the carrageenan pleurisy assay. Carrageenan pleurisy is induced as previously desbribed by Carter, G. W., et al., in J. Pharm. Pharmacol. 34:66–67, 1982. Carrageenan (310 μg/rat) is injected intrapleurally in a 0.25 ml volume of pyrogen-free saline. Four hours later, the rats are sacrificed and 2 ml of a phenol red solution (325 mg phenol red in 1 liter of 0.05M phosphate buffered saline) are added to each pleural cavity. The contents of the cavities are mixed and transferred to glass test tubes. A 50 μl aliquot is removed from each tube and exudate cells are counted after red blood cells lysis (with Zapoglobin; Coulter Electronics, Hialeah FL) using a Coulter model ZBI counter. The remaining exudatephenol red mixture is centrifuged at 750 xg for 15 minutes. One-hundred μl of the supernatent fluid is diluted with 3.9 ml of phosphate buffer (0.072M of tribasic sodium phosphate, $Na_3PO_4 \cdot 12H_2O$, in water) and the absorbance is measured at 560 nm.

Exudate volume is calculated as follows:

$$V_1 = \frac{V2(A_2 - A_3)}{(A_3 - A_1)}$$

where $V_1$=unknown volume of exudate, $V_2$=volume of dye added to cavity (2 ml), $A_1$=absorbance of exudate (assumed to be zero), $A_2$=absorbance of the phenol red solution, $A_3$=absorbance of exudate and phenol red solution.

Inhibition of exudate of formation is calculated by the following equations:

$$\% \text{ inhibition (exudate)} = \frac{\text{Vehicle Exudate Volume} - \text{Inhibitor Exudate}}{\text{Vehicle Exudate Volume}} \times 100$$

$$\% \text{ inhibition (cell count)} = \frac{\text{Vehicle Cell Count} - \text{Inhibitor Cell Count}}{\text{Vehicle Cell Count}} \times 100$$

$ID_{50}$ values are calculated by Probit analysis.

| Example | Dose mg/kg | % Inhibition Exudate | WBC |
|---|---|---|---|
| 21 | 1 | 20.6 | 26.9 |
|    | 3 | 38.3 | 49.7 |
| 24 | 10 | 24.7 | 38.3 |
|    | 70 | 65.6 | 79.8 |

Accordingly, the present invention also includes a pharmaceutical composition for treating psychoses pain, sleep disorders, inflammation, or hypertension comprising a corresponding antipsychotic analgesic, sleep inducing, antiinflammatory, or antihypertensive effective amount of a compound of the Formula I as defined above together with a pharmaceutically acceptable carrier.

The present invention further includes a method for treating psychoses, pain, sleep disorders, inflammation, or hypertension in mammals suffering therefrom comprising administering to such mammals either orally or parenterally a corresponding pharmaceutical composition containing a compound of the Formula I as defined above in appropriate unit dosage form.

For preparing oharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, stach, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

(R,S)-$N^6$-[1-Tetrahydronaphthyl]-adenosine

6-Chloropurine riboside (14.3 g, 50 mmol) was added, at once, to a stirred solution of tetrahydronaphthyl-1-amine. HCl (9.2 g, 50 mmol) and triethylamine (11.1 g, 110 mmol) in ethanol (300 ml). The solution was stirred at reflux for 18 hours. The solution was cooled to room temperature and water (300 ml) added to precipitate the compound. The precipitate was filtered and dried in vacuo at 45° C., overnight. The solid was purified by pressurized liquid chromatography, 1 column, eluting with 5% MeOH:CHCl$_3$, at 150 ml/min. One component was isolated by evaporation of the chromatography solvent. This was dried in vacuo at room temperature, overnight: yield 7.2 g (36%); m.p.=95.5°–100° C., 115°–120° C. Anal. (C$_{20}$H$_{23}$N$_5$O$_1$) Calcd: C=60.44, H=5.83, N=17.62, Found: C=59.95, H=5.63, N=17.53: HPLC (1 ml/min, C-18 analytical, 1:1 water:methanol) ret. times 72.18, 76.06; 49.8%, 50.2%. H$^1$NMR (DMSO-d$_6$, 60 MHz): δ1.95 (m, 4H), δ2.8 (m, 2H), δ3.65 (m, 2H), δ3.95 (m, 1H), δ4.15 (m, 1H), δ4.65 (m, 1H), δ5.15 (d, 1H), δ5.35 (br/t, 1H), δ5.4 (d, 1H), δ5.7 (br, 1H), δ5.9 (d, 1H), δ7.15 (s, 4H), δ8.0 (d, 1H), δ8.25 (s, 1H), δ8.35 (s, 1H).

EXAMPLE 2

(R)-$N^6$-[1-Tetrahydronaphthyl]-adenosine

6-Chloropurine riboside (2.0 g, 7 mmol) was added at once, to a solution of (R)-1-amino-tetralin[1].HCl (1.3 g, 7 mmol) and triethylamine (2.0 g, 20 mmol) in ethanol (100 ml). The solution was stirred at reflux for 18 hours. The solution was then cooled to room temperature and the solvent removed in vacuo. The residue was worked up with water (3×100 ml) and then coevaporated to dryness with methanol (5×100 ml). The resultant foam was dried under high vacuum at room temperature, overnight; yield 1.9 g (68%): m.p.=113°–115° C. HPLC (1 ml/min, C-18 analytical (1:1 water:methanol): ret. time 72.26, 100%. Anal. (C$_{20}$H$_{23}$N$_5$O$_4$), Calcd: C=60.44, H=5.83, N=17.62; Found: C=59.50, H=6.13, N=17.60. H$^1$NMR (DMSO-d$_6$, 200 MHz): δ1.73–2.0 (m, 4H), δ2.74 (br/s, 2H), δ3.47–3.71 (m, 2H), δ3.95 (m 1H), δ4.13 (m, 1H), δ4.62 (q, 1H), δ5.18 (d, 1H), δ5.38–5.46 (m, 2H), δ5.62 (br, 1H), δ5.88 (d, 1H), δ7.09 (s, 4H), δ8.09 (d, 1H), δ8.24 (s, 1H), δ8.35 (s, 1H).

EXAMPLE 3

(S)-$N^6$-[1-Tetrahydronaphthyl]-adenosine

6-Chloropurine riboside (0.6 g, 2.1 mmol) was added, at once, to a stirred solution of the S-1-amino-tetralin[1]. HCl (0.4 g, 2.18 mmol) and triethylamine (0.4 g, 4 mmol) in ethanol (60 ml).

[1] V. Ghisland; D. Vercesi; Il. Farmaco.-Ed Sc.; 26(S), 474–486 (1971).

The solution was warmed to reflux for 18 hours. The solution was then cooled to room temperature and a small amount of precipitate filtered and discarded. The solvents were removed in vacuo and the residue was purified by pressurized silica gel chromatography (1 column eluting with 5% MeOH:CH$_2$Cl$_2$, at 150 ml/min). One component was isolated by evaporation of the chromatography solvent; yield 0.45 g (54%): m.p.=117°–125° C.:HPLC (1 ml/min, C18 analytical, (1:1, water:methanol): ret. times 72.4, 76.4; 7.6%, 92.4%. Anal. (C$_{20}$H$_{23}$N$_5$O$_4$), Calcd: C=60.44, H=5.83, N=17.62; Found: C=59.46, H=6.07, N=17.52. H$^1$NMR (DMSO-d$_6$, 200 MHz): δ1.7–2.0 (m, 4H), δ2.75 (br.s, 2H), δ3.47–3.72 (m, 4H), δ3.95 (m, 1H), δ4.13 (m, 1H), δ4.61 (q, 1H), δ5.18 (d, 1H), δ5.43 (m, 2H), δ5.63 (br, 1H), δ5.88 (d, 1H), δ7.09 (s, 4H), δ8.09 (d, 1H), δ8.24 (s, 1H), δ8.35 (d, 1H).

EXAMPLE 4

$N^6$-[1-(2-Methyl)-tetrahydronaphthyl]-adenosine

A solution of 1-amino-2-methyl tetralin (2.76 g, 14 mmol), triethylamine (3.0 g, 30 mmol) and 6-chloropurine riboside (4.0 g, 14 mmol) in ethanol (250 ml) was stirred at reflux overnight. The solution was then cooled to room temperature and the ethanol removed in vacuo. The residue was washed twice with water (250 ml). The residue was coevaporated to dryness with ethanol (2×100 ml) to[1] give a foam. The foam was dissolved in 10% MeOH:CH$_2$Cl$_2$ (minimum amount) and purified by silica gel chromatography; yield 3.9 (68%): m.p.=126°-134° C. Anal (C$_{21}$H$_{25}$N$_5$O$_4$). Calcd: C=61.30, H=6.12, N=17.02; Found: C=61.31, H=6.22, N=16.84.

[1] V. Ghisland; D. Vercesi; Il. Farmaco.-Ed Sc.; 26(S), 474–486 (1971).

EXAMPLE 5

N$^6$-[1-(7-Methoxy)-tetrahydronaphthyl]-adenosine

A solution of the 1-amino-7-methoxy tetralin (6.1 g, 34.4 mmol), triethylamine (8.1 g, 80 mmol) and 6-chloropurine riboside (4.3 g, 15 mmol) in ethanol (100 ml) was warmed to reflux and stirred 48 hours. The solution was cooled to room temperature and the solvent removed in vacuo. The residue was twice washed with water and the residue coevaporated to dryness with methanol (4×100 ml) to give a light brown foam. The foam was purified by silica gel chromatography eluting with 10% MeOH:CH$_2$Cl$_2$. The major component was isolated by evaporation of the chromatography solvent and dried on high vacuum at room temperature, yield 3.9 g (61%): m.p.=95°-110° C. Anal (C$_{21}$H$_{25}$N$_5$O$_5$). Calcd: C=59.01, H=5.90, N=16.38; Found: C=58.70, H=6.11, N=16.32.

The starting material was prepared as follows:

A solution of 6-methoxy-tetralone (5 g, 28.4 mmol) in ethanol (50 ml) was treated with a solution of hydroxylamine.HCl (6.3 g, 90 mmol) and sodium acetate (7.4 g, 90 mmol) in water (50 ml). The new solution was warmed to reflux for four hours and cooled to room temperature. The ethanol was removed in vacuo and the residue was stirred into water. The precipitate was collected and dried in vacuo, yield 5.2 g (96%). The oxime (5.2 g, 27.2 mmol) was then reduced to the amine with 10% Rh/C in MeOH to give after evaporation of the solvent the crude amine, yield 6.1 g (125%).

EXAMPLE 6

N$^6$-[1-(6-Methoxy)-tetrahydronaphthyl]-adenosine

The title compound is prepared essentially as described in example 1, substituting 6-methoxy-1-aminotetralin for 1-aminotetralin; melting point 117°-120° C. Anal. (C$_{21}$H$_{25}$N$_5$O$_5$): Calcd: C=59.0, H=5.89, N=16.38; Found: C=58.49, H=6.04, N=16.21. H$^1$NMR (DMSO-d$_6$, 200 MHz): δ1.6-2.0 (br.m, 4H), δ2.7 (br.s, 2H), δ3.5-3.8 (br.m.+s, 5H), δ3.95 (d of d, 1H), δ4.15 (d of d, 1H), δ4.6 (d of d, 1H), δ5.2 (d, 1H), δ5.4 (m, 2H), δ5.6 (m, 1H), δ5.85 (d, 1H), δ6.7 (m, 2H), δ7.05 (m, 1H), δ7.95 (d, 1H), δ8.2 (br.s, 1H), δ8.3 (s, 1H).

The starting material was prepared as follows:

6-methoxy-1-tetralin oxime

A mixture of 11.28 g hydroxylamine hydrochloride and 13.3 g of sodium acetate, in 91 ml of water is added to a solution of 10 g of 6-methoxy-1-tetralone (Aldrich) in 82 ml of absolute ethanol. The mixture is stirred at reflux for one hour. The reaction is cooled to room temperature and the solid percipitate is filtered, washed with cold ethanol and dried, affording 9.05 g (83%) of the desired oxime having a melting point of 122°-124° C.

6-Methoxy-1-aminotetralin 9.05 g of the oxime is catalytically reduced by 1.0 g of 10% Rh/C in 50 ml methanol and 50 ml THF affording 7.8 g (93%) of the desired amine.

EXAMPLE 7

N$^6$-[5-Methoxy-1-aminotetralin]-adenosine

The title compound is prepared essentially as described in exmmple 1, substituting 5-methoxy-1-aminotetralin for 1-amino-tetralin; m.p. 87°-90° C. Analysis for (C$_{21}$H$_{25}$N$_5$O$_5$.½C$_3$H$_8$O) Calcd: C=59.07, H=6.38, N=15.31; Found: C=59.51, H=6.10, N=15.00. H$^1$NMR (DMSO-d$_6$, 200 MHz): δ1.6-2.05 (m, 4H), δ2.6 (br.s, 2H), δ3.5-3.8 (br.m.+s, 5H), δ3.95 (m, 1H), δ4.15 (m, 1H), δ4.6 (d of d, 1H), δ5.2 (m, 1H), δ5.4 (m, 2H), δ5.9 (d, 1H), δ6.8 (t, 2H), δ7.05 (t, 1H), δ8.05 (m, 1H), δ8.2 (br.s, 1H), δ8.3 (s, 1H).

The starting material was prepared as follows:

4.11 g (23.32 mmol) 5-Methoxytetralone was dissolved in 100 ml ethanol. 5.84 g (70.94 mmol) methoxyamine hydrochloride and 5.82 g (70.94 mmol) sodium acetate were dissolved in 500 ml water and added to the ketone solution. After refluxing four hours, the ethanol was removed and the aqueous solution extracted with chloroform. Concentration of the organic layer yielded the oxime ether m.p. 33°-34°, b.p. 193°.

4.64 g (2.26 mmol) 5-methoxy-1-methyloxime. ether tetralin was added to 50 ml anhydrous THF and cooled to 0° under a nitrogen atmosphere. 113 ml (5 equivalents) 1 N diborane (THF solution) was added dropwise. After stirring one hour, the reaction was quenched with methanol. The solvents were removed then 50 ml 6N HCl was added. After stirring ½ hour, the solution was made basic with potassium carbonate and extracted with ether. After drying, the volatiles are removed to afford 5-methoxy-1-amino-tetralin m.p. 22°-25° C. This material is used as is to prepare the title compound.

EXAMPLE 8

(R)-N$^6$-(7-methoxy-1-tetralinyl)-adenosine

The salt A as prepared below (5.8 g, 17.7 mmol) was hydrolyzed in 1N NaOH (100 ml) and isolated by extraction with CHCL$_3$ (3×75 ml) and evaporation of solution to give 3.1 g of free base. The free amine is dissolved in ethanol (15.0 ml) and triethylamine (4.0 g, 40 mmol) and 6-chloropurine riboside (3.6 g, 12.5 mmol) were added. The solution was heated to reflux for 24 hours. The ethanol was removed in vacuo and residue dissolved in 5% MeOH/CH$_2$Cl$_2$ and purified by preparative 500A chromatography (silica gel, 1 column, 200 ml/min.) to give a single refractive index observable fraction. The solvent was evaporated in vacuo and the residue dried on high vacuum at room temperature for one hour, to give 3.6 (68%) of a white solid; mp=128°-130° C. Analalysis for (C$_{21}$H$_{25}$N$_5$O$_5$.0.-2MeOH); Calcd: C=58.69, H=6.00, N=16.14; Found: C=58.32, H=5.68, N=16.38. [α]$_D$=−45.7 (c=0.87, DMF).

EXAMPLE 9

(S)-N$^6$-(7-methoxy-1-tetralinyl)-adenosine

The salt B as prepared below (5.2 g, 17.0 mmol) was hydrolyzed in 1N NaOH (100 ml) and isolated by extraction with chloroform and evaporation of solvent to give 2.6 g of free base. The free amine (2.6 g, 15 mmol), triethyl amine (2.0 g, 20 mmol) and 6-chloropurine riboside (3.4 g, 12 mmol) was warmed to reflux in ethanol (150 ml) overnight. The solution was evaporated until free of ethanol and the residue treated with water ($2\times 300$ ml) and water removed by decanting. The residue evaporated to dryness with MeOH ($4\times 100$ ml). The resultant foam was dried on high vacuum at 65° C., overnight, to give 4.6 g (90%) of a white solid, m.p. 171.5°–174° C. Analysis for ($C_{21}H_{25}N_5O_5.0.7MeOH$); Calcd: C=57.93, H=6.23, N=15.57; Found: C=58.13, H=6.05, N=15.54. $[\alpha]_D 32$ −67.5 (c=1.13, DMF).

The starting salts A and B for Examples 8 and 9 above are prepared as follows:

Resolution of 7-methoxy-1-tetralinylamine 7-methoxy-1-aminotetralin (56 g, 316 mmol) and L-(d)-(+)-tartaric acid (47.4 g, 316 mmol) are heated to reflux in water (800 ml) reduced in vacuo to ~250 ml and cooled to 0° C. to ppt, overnight. The precipitate collected by filtration and dried at 65° C. in vacuo six hours to give 63 g of white solid. The solid (62 g) is redissolved in water (300 ml) at 100° C. and cooled to 0° C. to ppt, overnight. The new precipitate collected by filtration and dried at 65° C. in vacuo six hours to give 33 g of white solid. The solid (32.5 g) was again recrystallized from water (250 ml) as before to give 15.7 g). The recrystallization was repeated three more times, see the following Table 1, to give 6.5 g of a white pure solid, salt A.

TABLE 1

| Recrystallization No. | Amount Solid Used | Amount Water | Amount Solid Isolated | $[\alpha]_D$ | mp °C. |
|---|---|---|---|---|---|
| 1 | — | 250 ml | 63 g | +2.83 (c 1.06, MeOH) | 180–185 |
| 2 | 62 g | 300 ml | 33 g | +20.0 (c 1.06, MeOH) | 198–200 |
| 3 | 32.5 g | 250 ml | 15.7 g | +31.7 (c 1.13, MeOH) | 200–207 |
| 4 | 15.2 g | 200 ml | 13.6 g | Insol in MeOH | 207–208 |
| 5 | 13.1 g | 100 ml | 10.5 g | Insol in MeOH | 206–207 |
| 6 | 10 g | 100 ml | 6.5 g | Insol in MeOH | 207–208 |

TABLE 2

| Recrystallization No. | Amount Solid Used | Amount Water | Amount Solid Isolated | $[\alpha]_D$ | mp °C. |
|---|---|---|---|---|---|
|  | — | 100 ml | 12 g | — | — |
| 2 | 12 g | 200 ml | 8.1 g | Insol in MeOH | 207.5–210 |
| 3 | 7.7 g | 75 ml | 6.9 g | 1.4 (c 0.97, MeOH) | 210–212 |
| 4 | 6.7 | 50 ml | 6.0 g | Insol in MeOH | 211–212 |

The amine (26 g, 0.146 mol) and D-(l)-(−)-tartaric-acid (22 g, 0.146 mol) were heated to reflux in 100 ml water and cooled to 0° C. to ppt, overnight. The amine salt was recrystallized as before according to Table 2 shown above to give 6.0 g of a pure white solid, salt B.

EXAMPLES 10 AND 11

(R,S)-5-Methoxy-1-aminotetralin was resolved by treating the free basee with one molar equivalent of R-N-acetyl-3,4-dimethoxyphenylalanine, and repeated recrystallization of the salts in ethanol.

(S)-5-Methoxy-1-aminotetralin-N-acetyl-3,4-diemethoxyphenylalanine salt m.p. 214°–215° C.

(R)-5-Methoxy-1-aminotetralin-N-acetyl-3,4-dimethoxyphenylalanine salt m.p. 199°–201° C.

The individual salts were taken to the free base and reacted with 6-chloropurine riboside as described in Example 2.

EXAMPLE 10

(S)-N<sup>6</sup>-[5-methoxy-1-aminotetralin]-adenosine m.p. 100°–101° C.

EXAMPLE 11

(R)-N<sup>6</sup>-[5-Methoxy-1-aminotetralin]-adenosine m.p. 227°–228° C.

EXAMPLE 12

N<sup>6</sup>-(1-tetralinyl)-2′,3′-O-isopropylidene-adenosine

N<sup>6</sup>-(1-tetralinyl)adenosine (15.0 g, 37.7 mmol), bis-p-nitrophenyl-phosphate hydrate (14.1 g, 41 mmol) and dimethoxy propane (42 ml) were stirred at room temperature, in acetone (300 ml), under $N_2$, overnight. The reaction was quenched with saturated sodium bicarbonate (100 ml) and the solution stirred for two hours. The acetone was removed in vacuo and the aqueous solution extracted with methylene chloride ($3\times 200$ ml). The organic solution was dried over $MgSO_4$ and the soluent removed in vccuo. The residue was dissolved in methanol and filtered through a Dowex Column ($1\times 8,400$ mesh) (sodium bicarbonate foam) and eluted with methanol (1 liter-total). The methanol was evaporated in vacuo to give a white foamy solid which was co-evaporated with acetone ($2\times 50$ mn) and dried on high vacuum at room temperature for three hours to yield 14.9 g (90%) of a white foam, mp 95–98. Analysis for ($C_{23}H_{27}N_5O_4.0.25$ acetone); Calcd: C=63.11, H=6.36, N=15.50; Found: C=63.47, H=6.48, N=15.45.

EXAMPLE 13

N<sup>6</sup>-(1-tetralinyl)-5′-benzoyladenosine

The isopropylidene analog as prepared in Example 12 (4.3 g, 10 mmol) was dissolved in pyridine (20 ml) and treated with benzoyl chloride (2.0 g, 15 mmol) and the solution stirred at room temperature, overnight. The pyridine was removed in vacuo and the residue dissolved in methylene chloride (100 ml). The organic was washed successively with 1N HCl (100 ml), water (100 ml) and a saturated salt solution (100 ml) and dried over $MgSO_4$. The solvent was removed in vacuo and the residue purified by prep 500A chromatography (1 column, 100 ml/min, EtOAc, silica gel) to give one major fraction (by refractive index). The solvent evaporated in vacuo to give 3.8 g of a white foam. The foam (2.8 g, 5.2 mmol) was then hydrolyzed in 50% formic acid (100 ml) at 50°–60° C. for six hours. The acids removed in vacuo and the residue coevaporated to dryness with methanol (3×50 ml). The resultant foam was purified by prep 500A chromatography (1 column, silica gel, 150 ml/min) to give one major fraction (by refractive index). This fraction was isolated by evaporation of acetone and dissolved in methylene chloride (100 ml). The organic was washed with water (100 ml) and dried over MgSO$_4$ and evaporated in vacuo to give a white foam which was dried on high vacuum for one hour to give 1.2 g (33%) of white solid, mp 107°–112° C. Analysis for ($C_{27}H_{27}N_5O_5.0.15CH_2Cl_2$); Calcd: C=63.40, H=5.35, N=13.62; Found: C=63.69, H=5.19, N=13.61.

EXAMPLE 14

N$^6$-(1-tetralinyl)-5'-O-(O-acetyssalicoyl)adenosine

The title compound was prepared essentially in the same manner as 5'-benzoyl from the isopropylidene (4.3 g, 10 mmol) and O-acetylsalicoyl chloride (2.6 g, 13 mmol). To give, after formic acid hydrolysis, 0.9 g (17%) of a white solid, mp 93°–98° C. Analysis for ($C_{29}H_{29}N_5O_7.0.6H_2O$); Calcd: C=61.07, H=5.34, N=12.28; Found: C=61.27, H=5.21, N=12.19.

EXAMPLE 15

N$^6$-(1-tetralinyl)-5'-acetyl-adenosine

The title compound was prepared essentially the same manner as the 5'-benzoyl analog from the isopropyliene (2.2 g, 5 mmol) and acetic anhydride (0.6 g, 6 mmol). This yielded, after formic acid hydrolysis, 0.55 g of a white solid, mp 87°–97° C. Analysis for ($C_{22}H_{25}N_5O_5.0.35MeOH$); Calcd: C=59.56, H=5.90, N=15.54; Found: C=59.75, H=5.95, N=15.53.

EXAMPLE 16

N$^6$-[1-(5-hydroxy)-tetrahydronaphthyl]-adenosine

The title compound is prepared essentially as described in Example 1, substituting 5-hydroxy-1-aminotetralin for 1-aminotetralin; melting point 136°–138° C. Analysis for ($C_{20}H_{23}N_5O_5 0.9H_2O$); Calcd: C=55.91, H=5.60, N=16.30; Found: C=55.90, H=5.62, N=15.94.

EXAMPLE 17

N$^6$-[1-(7-hydroxy)-tetrahydronaphthyl]-adenosine

The title compound is prepared essentially as described in Example 1, substituting 7-hydroxy-1-aminotetralin for 1-aminotetralin; melting point 145°–147° C. Analysis for ($C_{20}H_{23}N_5O_5$); Calcd: C=58.11; H=5.60; N=16.93; Found: C=58.11; H=6.11; N=16.35.

EXAMPLE 18

N$^6$-[1-(5,7-dimethyl)-tetrahydronaphthyl]-adenosine

The title compound is prepared as described in Example 1, substituting 5,7-dimethyl-1-aminotetralin for 1-aminotetralin; melting point 130°–132° C. Analysis for ($C_{22}H_{27}N_5O$; $O_40.5C_2H_5OH$); Calcd: C=61.59; H=6.74; N=15.61; Found: C=61.89; H=6.70; N=15.45.

EXAMPLE 19

N$^6$-14 1-tetralinyl-2',3',5'-triethylcarbonate-adenosine

N$^6$-1-tetralinyladenosine (3.9 g, 10 mmol) was placed in pyridine (25 ml) and treated, slowly at room temperature, with ethyl chloroformate (6.5 g, 60 mmol). The solution was stirred at room temperature, overnight. The pyridine was removed in vacuo and the residue dissolved in methylene chloride (100 ml) and washed successively with 1N HCl (100 ml), water (100 ml), and saturated brine solution (100 ml). The organic solution was dried over MgSO$_4$, filtered and the solvent removed in vacuo to give a colored foam. The foam was dissolved in EtOAc/CH$_2$Cl$_2$ (7:3) (25 ml) and purified by prep 500A chromatography (silica gel, 1 column, 150 ml/min). The fast running fraction was isolated by evaporation of solvents and the residue coevaporated once with acetone (30 ml) to give 1.6 g (26%) of a white foam; mp 60°–63° C. Analysis for ($C_{29}H_{35}N_5O_{10}0.75$ acetone); Calcd: C=57.11, H=6.06, N=10.66; Found: C=57.90, H=5.87, N=10.94. 'HNMR: δ1.1–1.25 (m, 9H); δ1.6–2.1 (m, 4H); δ2.7–2.8 (m, 2H); δ4.02–4.3 (m, 6H); δ4.4–4.5 (m, 3H); δ5.60–5.7 (m, 2H); δ5.99 (t, J=5.5 Hz, 1H); δ6.26 (d, J=5.3 Hz, 1H); δ7.15 (br.s, 4H), δ8.15 (d, J=9 Hz, 1H), δ8.25 (s, 1H), δ8.31 (s, 1H).

EXAMPLE 20

N$^6$-tetralinyl-5'-benzylether-adenosine

Step 1 N$^6$-tetralinyl-O-2',3'-isopropylidene-adenosine

Dimethoxy propane (100 ml), N$^6$-tetralinyladenosine (35.2 g, 89 mmol) and bis-p-nitrophenylphosphate hydrate (32.6 g, 96 mmol) were stirred under N$_2$ atmosphere at room temperature, overnight. The reaction mixture was quenched 0.5 saturated sodium bicarbonate solution (100 ml) and the acetone removed in vacuo. The aqueous solution was diluted with water (300 ml) and extracted with methylene chloride (400 ml). The organic was washed with water (400 ml) and dried over MgSO$_4$. The solvents were removed in vacuo and the residue dissolved in methanol (50 ml). The methanoline solution was passed through a plug of Dowex (1×8), ammonium bicarbonate form) and washed with methanol (400 ml). The combined methanol filtration were combined and evaporated in vacuo to dryness to give 30 g (78%) of a rose colored foam. Analysis for ($C_{23}HN_5O_4$); Calcd: C=63.14, H=6.22, N=16.01; Found: C=63.44, H=6.26, N=16.00.

Step 2 N$^6$-tetralinyl-5'-benzylethyl adenosine

The isopropylidene analog, as prepared above in 1, (5.4 g, 10.2 mmol) was placed in 50% formic acid (150 ml) and stirred at 50° C. for six hours. The acid/water was removed in vacuo and the residue dissolved in acetone (30 ml). The solution was purified by prep 500A chromatography (silica gel, 1 column, 150 ml/min.). The fast running fraction was isolated and evaporated in vacuo to give an oily semisolid. The semisolid was dissolved in methylene chloride and washed with saturated salt solution and then dried over MgSO$_4$. The solvents were evaporated in vacuo and coevaporated once with dry acetone (30 ml). The residue was dried on high vacuum for one hour to give 2.1 g (42%) of a white solid, mp 78°–84° C. Analysis for ($C_{27}H_{29}N_5O_4.0.75$ acetone); Calcd: C=66.15, H=6.36, N=13.19; Found: C=65.79, H=5.89, N=13.48.

EXAMPLE 21

N$^6$-[2,3-dihydro-1H-inden-1-yl]methyl adenosine

A mixture of 3.0 g of 6-chloropurine riboside, 2.0 g of 1-indanylmethylamine as prepared in Example A hereinafter and 3.18 g of triethylamine are refluxed in 75 ml of absolute ethanol under nitrogen for 24 hours. The reaction is cooled to room temperature, precipitated nucleoside is filtered, washed with ethanol and dried affording 2.78 g (67%) of $N^6$-[2,3-dihydro-1H-inden-1-yl]methyl-adenosine having a melting point of 137°-139° C. Anals. calcd. for $C_{20}H_{23}N_5O_4$; Found: C=60.44; H=5.83; N=17.62 C=60.81; H=5.70; N=17.35.

EXAMPLE 22

$N^6$-[1H-inden-3-yl]methyl adenosine

A reaction mixture of 1.4 g of 6-chloropurine riboside, 1.6 g of [1H-inden-3-yl]methylamine as prepared in Example E hereinafter and 1.5 g of triethylamine in 150 ml ethanol is refluxed for 24 hours. Volatiles are evaporated under reduced pressure and residue is purified on Prep-500A using one prepacked silica gel column and 10% methanoldichloromethane as an eluant at a rate of 150 ml/min. Evaporation of solvent from pure fractions affords 0.43 g (22%) of $N^6$-[1H-inden-3-yl]methyl adenosine having a melting point of 200°-202° C. Anals. calcd. for $C_{20}H_{21}N_5O_4.0.3$ $CH_3OH$; Found: C=60.20; H=5.53; N=17.29; C=60.49; H=5.44; N=17.25.

EXAMPLE 23

$N^6$-[1,2,3,4-tetrahydro-1-hydroxy-1-naphthalenyl]methyladenosine adenosine A reaction mixture of 1.7 g of 6-chloropurine riboside, 1.7 g of (1,2,3,4-tetrahydro-1-hydroxynaphthyl)-methyamine as prepared in Example B hereinafter and 2.0 g of triethylamine is refluxed in 150 ml ethanol for 24 hours. Volatiles are evaporated to dryness and residue is treated with 150 ml of cold water. Clear aqueous solution is decanted off. The water treatment is repeated twice followed by dissolving the residue in methanol and evaporating it to dryness. Co-evaporation several times with methanol affords solid material. It is dried under reduced pressure yielding 2.2 g (85%) of $N^6$-[1,2,3,4-tetrahydro-1-hydroxy-1-naphthalenyl]methyl adenosine having a melting point of 110°-115° C. Anals. calcd. for $C_{21}H_{25}N_5O_5.0.5$ $C_2H_5OH$, Found: C=58.65; H=6.26, N=15.55, C=59.27; H=6.34; N=15.53.

EXAMPLE 24

$N^6$-[3,4-dihydro-1-naphthalenyl]methyladenosine

The title compound is prepared essentially as described in Example 21 substituting [3,4-dihydro-1naphthyl]methylamine as prepared in Example F hereinafter for 1-indanylmethylamine having a melting point of 131°-134° C. Anals. calcd. for $C_{21}H_{23}N_5O_4$; Found: C=61.60; H=5.66; N=17.11; C=61.33; H=5.62; N=16.86.

EXAMPLE 25

$N^6$-[2,3-dihydro-1-hydroxy-1H-inden-1-yl]methyl adenosine

The title compound is prepared essentially as described in Example 23 substituting 1-(1-hydroxyindanyl)methylamine as prepared in Example C hereinafter for (1,2,3,4-tetrahydro-1-hydroxynaphthyl)methylamine in 55% yield having a melting point of 125°-127° C. Anals. calcd. for $C_{20}H_{23}N_5O_5 0.7$ $C_2H_5OH$ Found: C=57.67; H=6.15; N=15.71; C=58.04; H=5.94; N=15,45.

EXAMPLE 26

$N^6$-[1-benzocycloheptenyl)methyladenosine

The title compound is prepared essentially as described in Example 21 substituting (1-benzocycloheptenyl)methylamin as prepared in Example G hereinafter for 1-indanylmethylamine in 63% yield having a melting point of 165°-168° C. Anals. calcd. for $C_{22}H_{25}N_5O_40.6$ $H_2O$. Found: C=60.84; H=6.08; N=16.13, C=60.61; H=5.97; N=16.21.

EXAMPLE 27

$N^6$-[1-hydroxy-1-benzocycloheptyl)methyladenosine

The title compound is prepared essentially as described in Example 23 substituting (1-hydroxy-1-benzocycloheptyl)methylamine as prepared in Example D hereinafter for (1,2,3,4-tetrahydro-1-hydroxynaphthyl)-methylamine in 95% yield having a melting point of 177°-180° C. Anals. calcd. for $C_{22}H_{27}N_5O_5$. $C_2H_5OH$, Found: C=59.12; H=6.82; N=14.36. C=59.29; H=6.81; N=14.33.

EXAMPLE 28

$N^6$-[1-benzocycloheptyl)methyladenosine

The title compound is prepared essentially as described in Example 21 substituting (1-benzocycloheptyl)methyamine as prepared in Example H hereinafter for 1-indanylmethylamine in 77% yield having a melting point of 120°-125° C. Anals. calcd. for $C_{22}H_{27}N_5O_4.0.6$ $H_2O$; Found: C=60.56; H=6.52; N=16.05; C=60.74; H=6.72; N=15.82.

Preparation for the respective sidechain amines is described below.

EXAMPLE A 1-Indanylmethylamine

To a suspension of 32 g of 1-indane carboxylic acid in 50 ml of dry toluene, 94 g (58 ml) of thionyl chloride is added and the mixture is heated at 90° C. for four hours. The reaction is cooled to room temperature and excess thionyl chloride is removed under reduced pressure. The residual liquid is slowly poured into 150 ml of cold aqueous ammonium hydroxide. Precipitated solid is filtered, washed with water, and dried under reduced pressure affording 31.3 g (98%) of 1-indanecarboxamide having a melting point of 151°-154° C.

To a solution of 150 ml of diborane (1M in THF) in 250 ml of dry THF. Ten g of 1-indane carboxamide is slowly added. Reaction mixture is stirred at reflux for three hours, cooled to room temperature, and worked up by slowly adding 150 ml of 1N HCl. THF is distilled off under reduced pressure, the aqueous solution is brought to pH~13 by addition of NaOH. It is extracted with ethyl acetate (2×300 ml). The organic extract is washed with water (1×100 ml), dried over $MgSO_4$, filtered, and evaporated to dryness affording 6.5 g (71%) of 1-indanylmethylamine. It was used as is in the next reaction.

EXAMPLE B (1-Hydroxy-1,2,3,4-tetrahydronaphthyl)methylamine

Five and one-half g of trimethylsilylcyanide is added to a mixture of 7.3 g of 1-tetralone and 10 mg of zinc iodide. The mixture is stirred at room temperature overnight. It is dissolved in 25 ml dry THF and slowly added to a suspension of 2.3 g of lithium aluminumhydride in 40 ml of THF. Reaction is refluxed for three hours and upon cooling, carefully quenched with water. Precipitate is filtered and aqueous solution is diluted with 100 ml 1N NaOH. It was extracted with ether (3×100 ml), dried over anhydrous MgSO₄, filtered, and ether evaporated yielding an oil which solidifies upon standing giving 6.4 g (73%) of (1-hydroxy-1,2,3,4-tetrahydronaphthyl)methylamine.

EXAMPLE C 1-(1-hydroxy-indanyl)methylamine

The title compound is prepared essentially as described in Example B substituting 1-indanone for 1-tetralone in 60% yield.

EXAMPLE D (1-hydroxy-1-benzocycloheptyl)methylamine

The title compound is prepared essentially as described in Example B substituting 1-benzosuberene for 1-tetralone in 92% yield. The amine is used as is in the next reaction.

EXAMPLE E (1H-Indene-3-yl)methylamine.hydrochloride

Two and three-tenth g of 1-hydroxyindanylmethylamine is dissolved in 100 ml of ethanol saturated with HCl. Reaction mixture is refluxed overnight. It is cooled to room temperature and volatiles are evaporated under reduced pressure. The residue is stirred with 300 ml anhydrous ether. Precipitated solid is filtered and dried affording 2.2 g (85%) of the (1H-indene-3-yl)methylamine hydrochloride having a melting point of 245° C. decomp.

EXAMPLE F

[3,4-dihydro-1-naphthyl]methylamine.HCl

The title compound is prepared essentially as described in Example E substituting 1-hydroxytetrahydronaphthylmethylamine for 1-hydroxyindanylmethyl amine in 78% yield having a mp of 189°–191° C.

EXAMPLE G (1-benzocycloheptenyl)methylamine HCl

The title compound is prepared essentially as described in Example E substituting 1-hydroxybenzocycloheptyl methylamine for 1-hydroxyindanylmethylamine in 74% yield having a melting point of 197°–200° C.

EXAMPLE H (1-benzocycloheptyl)methylamine.HCl

One g of the amine HCl prepared in Example G is hydrogenated over 5% Pd/C in 100 ml methanol at room temperature and 50 psi for 21 hours. The catalyst is filtered, washed with methanol. Volatiles are removed under reduced pressure from the filtrate.

The residue is treated with 200 ml ether. Precipitated solid is filtered and dried affording 0.95 g (95%) of the amine.HCl having a melting point of 183°–185° C.

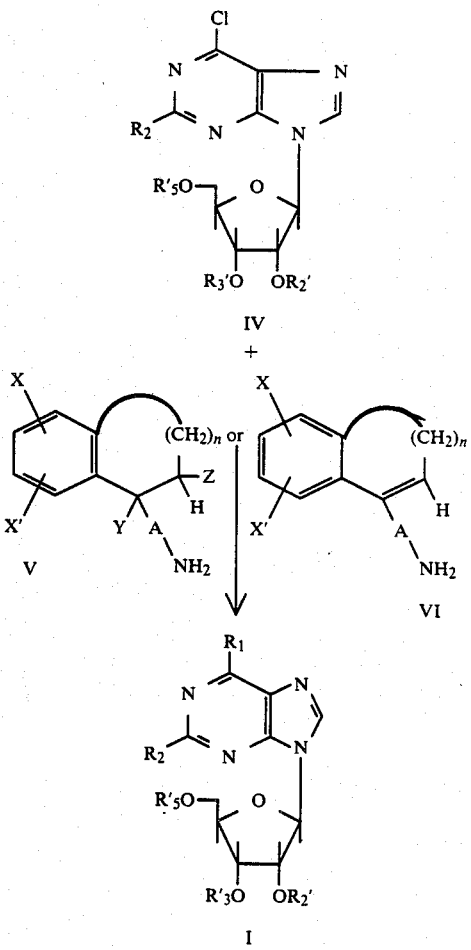

SCHEME I

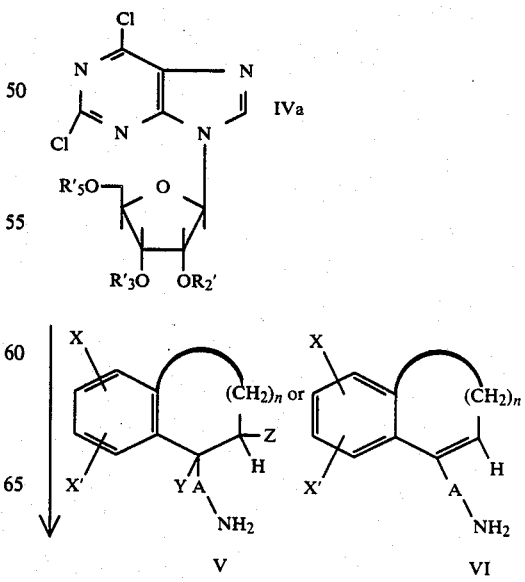

SCHEME II

SCHEME II

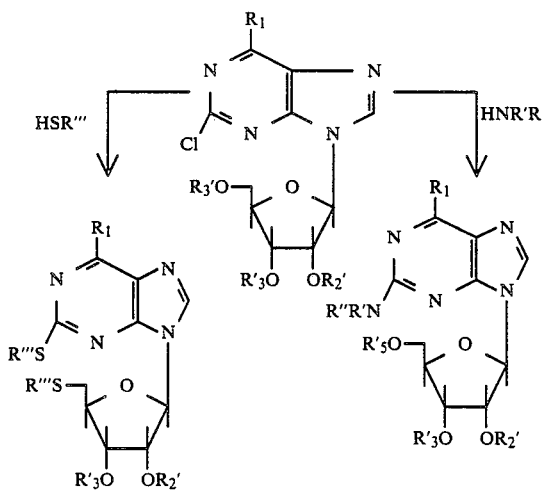

FORMULA

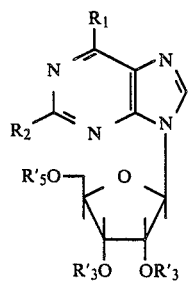

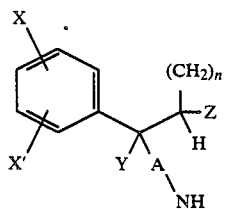

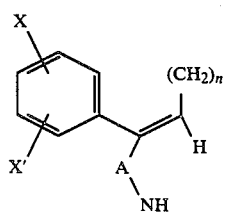

We claim:

1. A compound of the formula

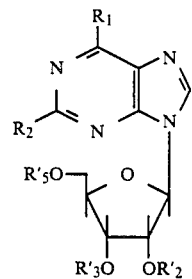

wherein $R_1$ is of the formula

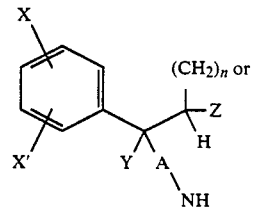

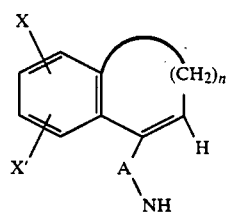

wherein n is one to four; Y is hydrogen, lower alkyl, or OR where R is hydrogen, lower alkyl or lower alkanoyl; A is a bond or a straight or branched alkylene of one to four carbon atoms, inclusive with the proviso that A cannot be a bond when $R_1$ is of Formula II and n is one; X and X' are each independently hydrogen, lower alkyl, lower alkoxy, hydroxy, lower alkanoyl, nitro, trifluoromethyl, halogen, amino, monoloweralkyl or diloweralkylamino, or when taken together a methylenedioxy group; $R_2$ is (a) hydrogen, (b) halogen, (c) NR'R" where R' and R" are independently hydrogen, lower alkyl, phenyl, or phenyl substituted by lower alkyl, lower alkoxy, halogen, or trifluoromethyl, (d) SR'" where R'" is hydrogen, lower alkyl, lower alkanoyl, benzoyl, or phenyl; $R'_2$, $R'_3$, and $R'_5$ are each independently hydrogen, alkanoyl having two to twelve carbon atoms, inclusive, in a straight or branched alkyl chain, benzoyl, or benzoyl substituted by lower alkyl, lower alkoxy, halogen, or $R'_2$ and $R'_3$ taken together are a five-membered ring having a total of up to twenty carbons; or $R'_5$ is independently a phosphate, hydrogen, or dihydrogen phosphate, or an alkali metal or ammonium, or dialkali or diammonium salt thereof; its diastereomer; or a pharmaceutically acceptable acid addition salt thereof; with the proviso that overall when $R_1$ is II and X, X', Y, and Z are hydrogen, or lower alkyl then n cannot be two.

2. A compound of claim 1 wherein $R_1$ is II wherein X, X', Y, Z, n, and A are as defined above.

3. A compound of claim 1 wherein $R_1$ is III wherein X, X', Y, Z, n, and A are as defined above.

4. A compound of claim 2 wherein Z is hydrogen, n is one and A is methylene.

5. A compound of claim 2 wherein Z is hydrogen, n is two to four carbon atoms, inclusive.

6. A compound of claim 2 wherein X, X', Y, and Z are hydrogen.

7. A compound of claim 3 wherein X, X', Y, and Z are hydrogen.

8. A compound of claim 6 wherein $R_2$ is hydrogen, chlorine, or amino and A is methylene.

9. A compound of claim 7 wherein $R_2$ is hydrogen, chlorine, or amino and A is methylene.

10. A compound according to claim 2 wherein A is a bond and n is 2.

11. A compound according to claim 10, wherein X and Y are hydrogen.

12. A compound according to claim 11, wherein Z is hydrogen or lower alkyl.

13. A compound according to claim 12, wherein $R_2$ is hydrogen.

14. A compound according to claim 13, wherein $R_2'$, $R_3'$, and $R_5'$ are each independently hydrogen, acetyl or benzoyl, or $R_2'$ and $R_3'$ when taken together are isopropylidene.

15. A compound according to claim 14, wherein $R_2'$, $R_3'$, and $R_5'$ are hydrogen.

16. A compound according to claim 15 and being (R,S)$N^6$-(1-tetrahydronaphthyl)-adenosine.

17. A compound according to claim 15 and being (R)$N^6$-[1-tetrahydronaphthyl]-adenosine.

18. A compound according to claim 15 and being (S)$N^6$-[1-tetrahydronaphthyl]adenosine.

19. A compound according to claim 15 and being $N^6$-[1-(2-methyl)tetrahydronaphthyl]adenosine.

20. A compound according to claim 15 and being $N^6$-[1-(7-methoxy)tetrahydronaphthyl]adenosine.

21. A compound according to claim 15 and being $N^6$-[1-(6-methoxy)tetrahydronaphthyl]adenosine.

22. A compound according to claim 15 and being $N^6$-[5-methoxy-1-aminotetralin]adenosine.

23. A compound according to claim 15 and being (R)$N^6$-(7-methoxy-1-tetralinyl)adenosine.

24. A compound according to claim 15 and being-(S)-$N^6$-(7-methoxy-1-tetralinyl)adenosine.

25. A compound according to claim 15 and being(S)-$N^6$-(5-methoxy-1-aminotetralin)adenosine.

26. A compound according to claim 15 and being (R)$N^6$-(5-methoxy-1-aminotetralin)adenosine.

27. A compound according to claim 14 and being $N^6$-(1-tetralinyl)-2', 3'-O-isopropylidene adenosine.

28. A compound according to claim 14 and being $N^6$-(1-tetralinyl)-5'-benzoyladenosine.

29. A compound according to claim 13 and being $N^6$-(1-tetralinyl)-5'-O-acetylsalicoyladenosine.

30. A compound according to claim 14 and being $N^6$-(1-tetralinyl)-5'-benzylether-adenosine.

31. A compound according to claim 15 and being $N^6$-[1-(5-hydroxy)tetrahydronaphthyl]-adenosine.

32. A compound according to claim 15 and being $N^6$-[1-(7-hydroxy)-tetrahydronaphthyl]adenosine.

33. A compound according to claim 15 and being $N^6$-[1-(5,7-dimethyl)tetrahydronaphthyl]-adenosine.

34. A compound according to claim 15 and being $N^6$-1-tetralinyl-2',3',5',-triethylcarbonate adenosine.

35. A compound according to claim 14 and being $N^6$-tetralinyl-5'-benzylether adenosine.

36. A compound of claim 4 wherein the specific embodiment is $N^6$-[2,3-dihydro-1H-inden-1-yl]methyladenosine. adenosine.

37. A compound of claim 6 wherein the specific embodiment is $N^6$-[1-benzocycloheptyl)methyladenosine. adenosine.

38. A compound of claim 7 wherein the specific embodiment is $N^6$-[1H-inden-3-yl]methyladenosine.

39. A compound of claim 7 wherein the specific embodiment is $N^6$-[3,4-dihydro-1-naphthalenyl]methyladenosine.

40. A compound of claim 7 wherein the specific embodiment is $N^6$-[1-benzocycloheptenyl)methyladenosine.

41. A compound of claim 2 wherein X and X' are hydrogen and Y is hydroxy.

42. A compound of claim 41 wherein the specific embodiment is $N^6$-[1,2,3,4-tetrahydro-1-hydroxy-1-naphthalenyl]methyladenosine.

43. A compound of claim 41 wherein the specific embodiment is $N^6$-[2,3-dihydro-1-hydroxy-1H-inden-1-yl]methyladenosine.

44. A compound of claim 41 wherein the specific embodiment is $N^6$-[1-hydroxy-1-benzocycloheptyl)methyladenosine.

45. A pharmaceutical composition comprising a therapeutically effective amount of a compound as claimed in claim 1 together with a pharmaceutically acceptable carrier.

46. A method for treating psychosis in a mammal suffering therefrom comprising administering to such mammal a compound as claimed in claim 1 in unit dosage form.

47. A method for treating hypertension in a mammal suffering therefrom, which comprises administering to such mammals a compound as claimed in claim 1 in unit dosage form.

48. A method for treating immunoinflammation in a mammal suffering therefrom, which comprises administering to such mammal a compound as claimed in claim 1 in unit dosage form.

* * * * *

UNITED STATES PATENT AND TRADEMARK OFFICE
CERTIFICATE OF CORRECTION

PATENT NO. : 4,791,103
DATED : December 13, 1988
INVENTOR(S) : B.K. Trivedi et al It is certified that error appears in the above—identified patent and that said Letters Patent is hereby corrected as shown below:

In column 28, lines 15-20

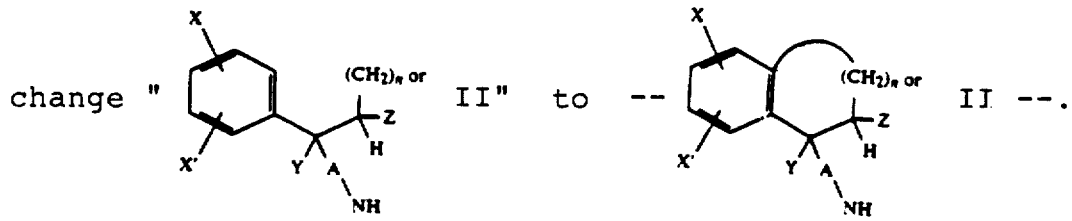

In column 30, line 13 after "thyladenosine." delete "adenosine."

Signed and Sealed this

Twenty-seventh Day of June, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,791,103

DATED : December 13, 1988

INVENTOR(S) : Bharat K. Trivedi, et al.

Page 1 of 3

It is certified that error appears in the above-identified patent and that said Letters Patent is hereby corrected as shown below:

In column 21, line 15 change      "$N^6$-(1-tetralinyl)-5'-O-(O-acetyssalicoyl) adenosine"

to      --$N^6$-(1-tetralinyl)-5'-O-(O-acetylsalicoyl)adenosine--.

In column 21, line 65 change      "$N^6$-14 1-tetralinyl-2',3',5'-triethylcarbonate-adenosine"

to      --$N^6$-1-tetralinyl-2',3',5',-triethylcarbonate-adenosine--.

UNITED STATES PATENT AND TRADEMARK OFFICE
CERTIFICATE OF CORRECTION

Page 2 of 3

PATENT NO. : 4,791,103

DATED : December 13, 1988

INVENTOR(S) : BHARAT K. TRIVEDI, ET AL.

It is certified that error appears in the above—identified patent and that said Letters Patent is hereby corrected as shown below:

In column 27, lines 45-65 change

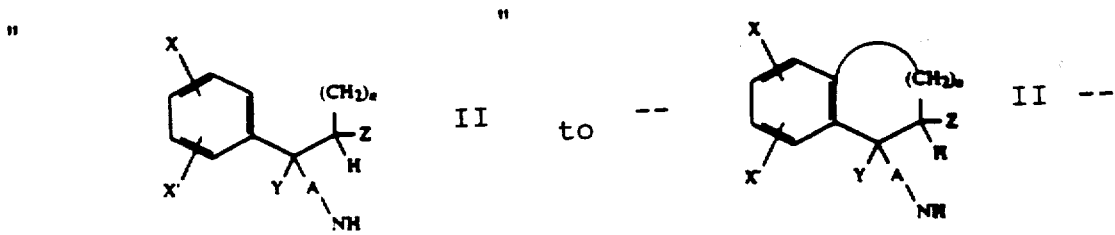

UNITED STATES PATENT AND TRADEMARK OFFICE
CERTIFICATE OF CORRECTION

PATENT NO. : 4,791,103  
DATED : December 13, 1988  
INVENTOR(S) : BHARAT K. TRIVEDI, ET AL.

Page 3 of 3

It is certified that error appears in the above-identified patent and that said Letters Patent is hereby corrected as shown below:

and change

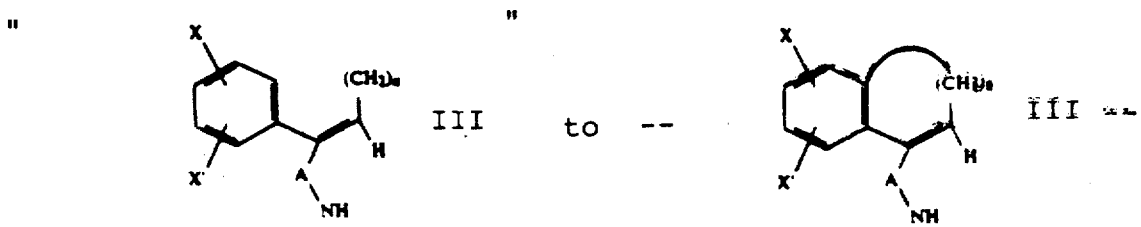

Signed and Sealed this

Fourth Day of June, 1991

Attest:

HARRY F. MANBECK, JR.

Attesting Officer

Commissioner of Patents and Trademarks